(12) United States Patent
Neal et al.

(10) Patent No.: US 6,634,750 B2
(45) Date of Patent: Oct. 21, 2003

(54) TOMOGRAPHIC WAVEFONT ANALYSIS SYSTEM AND METHOD OF MAPPING AN OPTICAL SYSTEM

(75) Inventors: Daniel R. Neal, Tijeras, NM (US); Richard J. Copland, Albuquerque, NM (US)

(73) Assignee: WaveFront Sciences, Inc., Albuquerque, NM (US)

( * ) Notice: Subject to any disclaimer, the term of this patent is extended or adjusted under 35 U.S.C. 154(b) by 0 days.

(21) Appl. No.: 10/167,439

(22) Filed: Jun. 13, 2002

(65) Prior Publication Data

US 2003/0038921 A1 Feb. 27, 2003

Related U.S. Application Data

(63) Continuation of application No. PCT/US02/07573, filed on Mar. 14, 2002.
(60) Provisional application No. 60/275,626, filed on Mar. 15, 2001.

(51) Int. Cl.[7] .................................. A61B 3/10
(52) U.S. Cl. ..................................... 351/211
(58) Field of Search ................. 351/205, 206, 351/211, 212, 221, 246; 356/124

(56) References Cited

U.S. PATENT DOCUMENTS

| | | |
|---|---|---|
| 3,819,256 A | 6/1974 | Bellows et al. |
| 4,021,102 A | 5/1977 | Iizuka |
| 4,725,138 A | 2/1988 | Wirth et al. |
| 4,838,679 A | 6/1989 | Bille |
| 5,062,702 A | 11/1991 | Bille |
| 5,258,791 A | 11/1993 | Penney et al. |
| 5,493,391 A | 2/1996 | Neal et al. |
| 5,777,719 A | 7/1998 | Williams et al. |
| 5,822,035 A | 10/1998 | Bille |

(List continued on next page.)

FOREIGN PATENT DOCUMENTS

| | | |
|---|---|---|
| DE | 42 22 395 A1 | 1/1994 |
| EP | 0 373 788 A2 | 6/1990 |
| EP | 0 625 332 A2 | 11/1994 |
| WO | WO 83/02716 | 8/1983 |
| WO | WO 00/10448 | 3/2000 |
| WO | WO 01/28408 A2 | 4/2001 |
| WO | WO 01/78585 | 10/2001 |
| WO | WO 01/82228 A2 | 11/2001 |
| WO | WO 01/89372 A2 | 11/2001 |

OTHER PUBLICATIONS

Geary, Joseph M., Introduction to Wavefront Sensors, SPIE Press, vol. TT18, copyright 1995, pp. 93–95.

Brown, et al., Measurement of the dynamic deformation of a high frequency scanning mirror using a Shack–Hartmann wavefront sensor; SPIE's 46th Annual Meeting International Symposium on Optical Science and Technology Jul. 29–Aug. 3, 2001; pp. 1–9.

(List continued on next page.)

Primary Examiner—George Manuel

(57) ABSTRACT

A method of measuring aberrations of a three-dimensional structure of an optical system, such as an eye, includes creating a plurality of light beams, optically imaging the light beams and projecting the light beams onto different locations in an optical system, receiving scattered light from each of the locations, and detecting individual wavefronts of the scattered light. The plurality of light beams may be created and projected simultaneously or sequentially. A system for measuring aberrations of a three-dimensional structure of an optical system includes a light source creating a plurality of light beams, an optical imaging system optically imaging the light beams and projecting the light beams onto different locations in the target optical system, and a wavefront sensor receiving scattered light from each of the locations and detecting individual wavefronts of the scattered light.

70 Claims, 10 Drawing Sheets

U.S. PATENT DOCUMENTS

| | | | |
|---|---|---|---|
| 5,920,373 | A | 7/1999 | Bille |
| 5,929,970 | A | 7/1999 | Mihashi |
| 5,936,720 | A | 8/1999 | Neal et al. |
| 5,949,521 | A | 9/1999 | Williams et al. |
| 5,978,053 | A | 11/1999 | Giles et al. |
| 6,007,204 | A | 12/1999 | Fahrenkrug et al. |
| 6,050,687 | A | 4/2000 | Bille et al. |
| 6,052,180 | A | 4/2000 | Neal et al. |
| 6,095,651 | A | 8/2000 | Williams et al. |
| 6,130,419 | A | 10/2000 | Neal |
| 6,155,684 | A | 12/2000 | Bille et al. |
| 6,199,986 | B1 | 3/2001 | Williams et al. |
| 6,270,221 | B1 | 8/2001 | Liang et al. |
| 6,271,914 | B1 | 8/2001 | Frey et al. |
| 6,271,915 | B1 | 8/2001 | Frey et al. |
| 6,299,311 | B1 | 10/2001 | Williams et al. |
| 6,382,795 | B1 | 5/2002 | Lai |
| 6,394,605 | B1 | 5/2002 | Campin et al. |
| 6,406,146 | B1 * | 6/2002 | Lai ............................ 351/206 |
| 6,550,917 | B1 * | 4/2003 | Neal et al. .................. 351/221 |

OTHER PUBLICATIONS

Neal et al., AIAA 98–2701 Shack–Hartmann wavefront sensor testing of aero–optic phenomena; 20th AIAA Advanced Measurement and Ground Testing Technology Conference Jun. 15–18, 1998, pp. 1–13.

Daniel R. Neal et al.; Application of Shack–Hartmann Wavefront Sensors to Optical System Calibration and Alignment; pp. 234–240.

Daniel R. Neal et al.; Characterization of Infrared Laser Systems; SPIE 3437–05 (1998); pp. 1–11.

Daniel R. Neal et al.; Amplitude and phase beam characterization using a two–dimensional wavefront sensor; SPIE vol. 2870, 0–8194–2267–3/96; pp. 72–82.

Daniel R. Neal et al.; Use of beam parameters in optical component testing; 4451, pp. 394–405.

D.R. Neal et al.; Wavefront sensors for optical diagnostics in fluid mechanics: application to heated flow, turbulence and droplet evaporation; SPIE vol. 2005, 0–8194–1254–6/93; pp. 194–203.

Lindlein et al.; Algorithm for expanding the dynamic range of a Shack–Hartmann sensor by using a spatial light modulator array; Optical Engineering, vol. 40 No. 5 May 2001; pp. 837–840.

Suzuki et al.; Error analysis of a Shack–Hartmann wavefront sensor; SPIE vol. 2443, 0–8194–1792–0/95; pp. 798–805.

Platt et al.; History and Principles of Shack–Hartmann Wavefront Sensing; Journal of Refractive Surgery, vol. 17, Sep./Oct. 2001; pp. S573–S577.

Lindlein, et al.; Experimental results for expanding the dynamic range of Shack–Hartmann sensor using astigmatic microlenses; Optical Engineering, vol. 41 No. 2, Feb. 2002; pp. 529–533.

Lindlein et al.; Absolute sphericity measurement: a comparative study of the use of interferometry and a Shack-–Hartmann sensor; Optics Letters/vol. 23, No. 10/May 15, 1998; pp. 742–744.

Lindlein et al.; Dynamic range expansion of a Shack–Hartmann sensor by use of a modified unwrapping algorithm; Optics Letters/vol. 23, No. 13/Jul. 1, 1998; pp. 995–997.

L. McMackin, B. Masson, N. Clark, K. Bishop, R. Pierson, E. Chen, Hartmann Wave Front Sensor Studies of Dynamic Organized Structure in Flowfields, AIAA Journal, 33 (11) pp. 2158–2164 (1995).

Liang, et al., Hartmann–Shack Sensor as a Component in Active Optical System to Improve the Depth Resolution of the Laser Tomographic Scanner, SPIE 1542, pp. 543–554 (1991).

David A. Goss and Roger W. West, Introduction to the Optics of the Eye, (2002).

* cited by examiner

TOMOGRAPHIC WAVEFONT ANALYSIS SYSTEM AND METHOD OF MAPPING AN OPTICAL SYSTEM

CROSS REFERENCE TO RELATED APPLICATIONS

This is a continuation application claiming the priority benefit under 35 U.S.C. §119 of International Application Ser. No. PCT/U502/07573 filed on Mar. 14, 2002, and U.S. Provisional Patent Application No. 60/275,626 filed on Mar. 15, 2001, the entirety of each of which is hereby incorporated by reference for all purposes as if frilly set forth herein.

BACKGROUND AND SUMMARY OF THE INVENTION

1) Field of the Invention

This invention pertains to the field of measurements of refractive errors in an optical system, and more particularly to systems and methods for compiling a tomographic mapping of the refractive errors in an optical system such as the eye.

2) Description of the Related Art

Measurements of aberrations of the eye are important for the diagnosis of visual defects and acuity. There are a growing number of ways that aberrations can be corrected using both surgical and non-surgical means. These methods rely on accurate, precise measurements of the whole ocular system so that patients may be screened, the corrective means applied and tested, and followed up as appropriate. In addition, an enhancement to the accuracy and precision of ocular measurements may lead to improved methods for correcting visual defects, and for identifying patients in need of care.

There are a number of existing methods used to measure the performance of the ocular optical system. The best established are psychophysical methods, which rely on subjective patient feedback to for the parameters of the measurement. The oldest of these is the phoropter or trial lens method. This technique relies on a trial and error method to identify the required correction. There are psychophysical techniques for measuring visual acuity, ocular modulation transfer function, contrast sensitivity and other parameters of interest. Such techniques are disclosed, for example, in DAVID A. GOSS AND ROGER W. WEST, INTRODUCTION TO THE OPTICS OF THE EYE (2002).

In addition to the subjective methods, there are number of objective means for measuring the performance of the ocular system. These include corneal topography, wavefront aberrometry, corneal interferometry, auto-refraction, and numerous other means for measuring the eye. These methods may be summarized as described below.

The surface shape and thickness of the cornea are extremely important information for laser vision correction surgery, inter-ocular contacts, radial keratotomy, and other surgical repair and correction schemes. Comeal topography can measure the surface shape of the cornea. Corneal topography can be used to measure the deviation of the corneal shape from the ideal shape required for perfect vision. There are several commercial instruments that use different methods to accomplish this. Many of these methods operate on the cornea directly, and thus its thickness, shape and other parameters are critical to obtaining good results. U.S. Pat. Nos. 4,838,679, 5,062,702, 5,822,035, and 5,920,373 to BILLE disclose mapping the cornea of an eye using a variety of methods. The cornea has enough of a difference in index of refraction between the front and rear surfaces that it is possible to also measure the corneal thickness.

However, the cornea only partially contributes to the optical errors of the ocular system. Many other elements, such as vitreous fluid and the crystalline lens may also be significant factors that are not accounted for by corneal topography.

Another instrument for objectively determining the refraction of the eye is the auto-refractor. The auto-refractor uses one of various means to automatically determine the required corrective prescription. This may consist of the projection of one or more spots or patterns onto the retina. Through adjustment of various optical elements in the auto-refractor instrument, the required correction is automatically detected. Numerous auto-refractors have been developed and are in common clinical use. Examples may be found in U.S. Pat. Nos. 3,819,256 and 4,021,102.

However, the accuracy of the refraction is often suspect, and eye doctors rarely use this information without further refinement. The basic problem with the auto-refractor is that it measures only lower order components of the aberrations, such as the spherical and astigmatic errors. Higher order aberrations are not accounted for by the auto-refractor. Only the average performance of the optical system is measured by the auto-refractor.

Recently, there has been attention focused on treatment of the eye as an optical system. This has lead to the application of methods for measuring the eye that have previously been used for other optical systems, e.g., interferometry, Shack-Hartmann wavefront sensing. These techniques are extremely powerful because they measure the complete aberrations of the eye's optical system.

In wavefront aberrometry, a spot is projected on the retina of the eye and then the resulting scattered light is measured with an optical system. The full, end-to-end integrated line of sight, measurement of the aberrations of the eye is obtained. Thus, wavefront aberrometry can be used to measure the full aberration content of the optical system of the eye from end to end.

This additional information allows researchers and clinicians to measure non-symmetric, non-uniform effects that may be affecting vision. In addition, the information can be linked directly to many of the various corrective means to provide greatly improved vision for many patients.

U.S. Pat. No. 5,777,719 to WILLIAMS describes the application of Shack-Hartmann wavefront sensing and adaptive optics for determining the ocular aberrations to make a super-resolution retina-scope. This information is then used to make better contact lenses, inter-ocular lenses and other optics as disclosed in U.S. Pat. No. 5,949,521 to WILLIAMS. PCT patent publication WO 00/10448 by AUTONOMOUS TECHNOLOGIES discloses refined methods for projecting the light beam onto the retina. U.S. Pat. No. 6,007,204 to ALLYN WELCH discloses a simplified hand held unit. Commonly owned, co-pending U.S. patent application Ser. No. 09/692,483 (Attorney Docket No. WFS.006) to NEAL ET AL. discloses an integrated instrument that uses an improved projection system to minimize the size of the spot on the back of the eye, and thus allow much higher resolution wavefront sensing.

As described above, corneal topography can be used to measure the deviation of the corneal shape from the ideal shape required for perfect vision, and wavefront aberrometry can be used to measure the full aberration content of the optical system from end to end. However, for most surgical (and some non-surgical) procedures, knowledge of both the corneal shape and the wavefront aberrations is needed. This can be accomplished by measuring the same eye successively with both a wavefront aberrometer and a corneal topographic instrument, or by making these measurements with a combined instrument. U.S. Pat. No. 6,050,687 to BILLE discloses a method for integrating both corneal topographic and wavefront aberration functions into a single device.

The objective of such a combined instrument is to identify not only the aberration content of the eye, but to separate the effects of the various contributors. Roughly 30% of the aberration is known to be due to corneal shape. Thus the remaining 70% is due to other, buried structures. Wavefront aberrometry does not provide a measure of the three-dimensional structure of the index of refraction field. Combining wavefront aberrometry with corneal topography allows the user to determine the contribution due to the surface, but does not identify any other source.

What is really needed is a means for measuring not only the aberrations of individual structures, but also the full three-dimensional structure of an eye or other optical system.

The measurement of three-dimensional structures interior to a media is a difficult, if often studied, problem. For human biological systems, a non-invasive procedure is required. This limits the methods that are available. Since the eye can be probed only from the front (without extensive surgical methods), there is a natural limit to what can be measured. This problem is encountered in x-ray radiology, where internal organ or skeletal structure is studied. There are a number of techniques that have been applied to this field, the most notable of which are nuclear magnetic resonance (NMR) and computed automated tomography (CAT). These two techniques are eminently successful in measuring buried three-dimensional structures in the human body, and are routinely applied around the world. NMR relies on introducing a magnetic modulation in the molecular and atomic structure of certain elements in the body, and observing the response. It uses the geometric intersection of a plane and a line to determine the three-dimensional structure of the object under study. Computed automated tomography uses a series of projected measurements that are line-integrals through the object under study to de-convolve the original structure.

Wavefront sensing is a line-of-sight measurement technique. The principles of computed automated tomography may be applied to reconstruct the three-dimensional structure of an object from multiple views or measurements of the object obtained by wavefront sensing. This technique has been applied to measure three-dimensional structures in a fluid jet. To this end, eight linear wavefront sensors have been employed to simultaneously acquire high-speed data. A full three-dimensional flow field of the dynamic turbulent jet was reconstructed using this technique (see L. McMackin, B. Masson, N. Clark, K. Bishop, R. Pierson, and E. Chen, *Hartmann Wave Front Sensor Studies of Dynamic Organized Structure in Flow Fields*, AIAA JOURNAL, 33 (11) pp. 2158–2164 (1995)).

However, many extensions, variations and extrapolations to the system and techniques employed for measuring the fluid jet are required in order to measure a living eye or other optical system.

In Liang, et al., *Hartmann-Shack Sensor as a Component in Active Optical System to Improve the Depth Resolution of the Laser Tomographic Scanner*, SPIE 1542, pp. 543–554 (1991), use of adaptive optics to improve the resolution of an instrument used to make measurements near the retina is reported. A laser tomographic scanner is used to measure the retina. However, the wavefront sensor and adaptive optics system of Liang, et al. is only employed to improve the resolution of the scanner.

Accordingly, it would be advantageous to provide a system capable of measuring not only the aberrations of the individual structures, but also the full three-dimensional structure of the eye or other optical system. It would also be advantageous to provide a method of measuring the aberrations of the full three-dimensional structure of the eye or other optical system. Other and further objects and advantages will appear hereinafter.

The present invention comprises a method and system for performing optical system measurements that overcome at least one of the above disadvantages.

It is an object of this invention to determine the three dimensional structure of the eye or other optical system. This may be realized by projecting multiple spots onto a retina in such a manner that the wavefront aberration resulting from each spot may be separately determined, either simultaneously or sequentially. This group of wavefront aberration maps may then be analyzed using the methods of computed automated tomography to determine the three dimensional structure of the eye or other optical system. These and other objects of the present invention will become more readily apparent from the detailed description given hereinafter.

In one aspect of the invention, a tomographic wavefront analysis system comprises a projection system creating a plurality of collimated light beams; an optical imaging system receiving the plurality of collimated light beams and simultaneously providing the plurality of collimated light beams onto a plurality of different locations in an eye; and a wavefront sensor simultaneously receiving scattered light from each of the different locations.

In another aspect of the invention, a method of measuring aberrations of a three-dimensional structure of an optical system includes creating a plurality of collimated light beams, simultaneously providing the plurality of collimated light beams onto a plurality of different locations in the optical system, and simultaneously receiving scattered light from each of the different locations.

In yet another aspect of the invention, a tomographic wavefront analysis system comprises a projection system creating a light beam and scanning the light beam in a plurality of desired directions, an optical imaging system receiving the scanned light beam and providing the scanned light beam onto a plurality of different locations in an eye, and a wavefront sensor receiving scattered light from each of the different locations.

In still another aspect of the invention, a method of measuring aberrations of a three-dimensional structure of an optical system includes creating a light beam and scanning the light beam in a plurality of desired directions, providing the scanned light beam onto a plurality of different locations in an optical system, and receiving scattered light from each of the different locations.

In a further aspect of the system, a wavefront sensor for a wavefront analysis system, comprises a lenslet array receiving and focusing scattered light and a plurality of detector arrays located at different detector planes for detecting the focused scattered light from the lenslet array, wherein each of the detector arrays is color-coded to substantially detect only light corresponding to a different corresponding wavelength.

In a still further aspect of the invention, a lenslet array receiving and focusing scattered light and a detector array having a mosaic pattern of color-coded pixels detecting the focused scattered-light.

In yet another aspect of the invention, a corneal topography measurement can be incorporated along with the tomographic wavefront analysis system. The corneal topographer can be any of several designs, the placido disc system being the representative type of that system. The mathematical reduction of the data uses data from placido discs or the light emitting diodes or other arrangement to determine the surface shape of the cornea. Then the tomographic wavefront analysis system is used to mathematically determine the internal three dimensional structures of the eye.

However, it should be understood that the detailed description and specific examples, while indicating the preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

Embodiments and other aspects of the invention described herein, including the system embodiments described below, may be made or used in conjunction with inventions described, in whole or in part, in co-pending U.S. patent application Ser. No. 09/692,483 filed on Oct. 20, 2000 in the name of inventors Daniel R. Neal, Darrell J. Armstrong, James K. Gruetzner, and Richard J. Copland entitled "DYNAMIC RANGE EXTENSION TECHNIQUES FOR A WAVEFRONT SENSOR INCLUDING USE IN OPHTHALMIC MEASUREMENT"(hereinafter "the WFS.006 Application") which is hereby incorporated herein by reference for all purposes as if fully set forth herein.

Figure 1A:
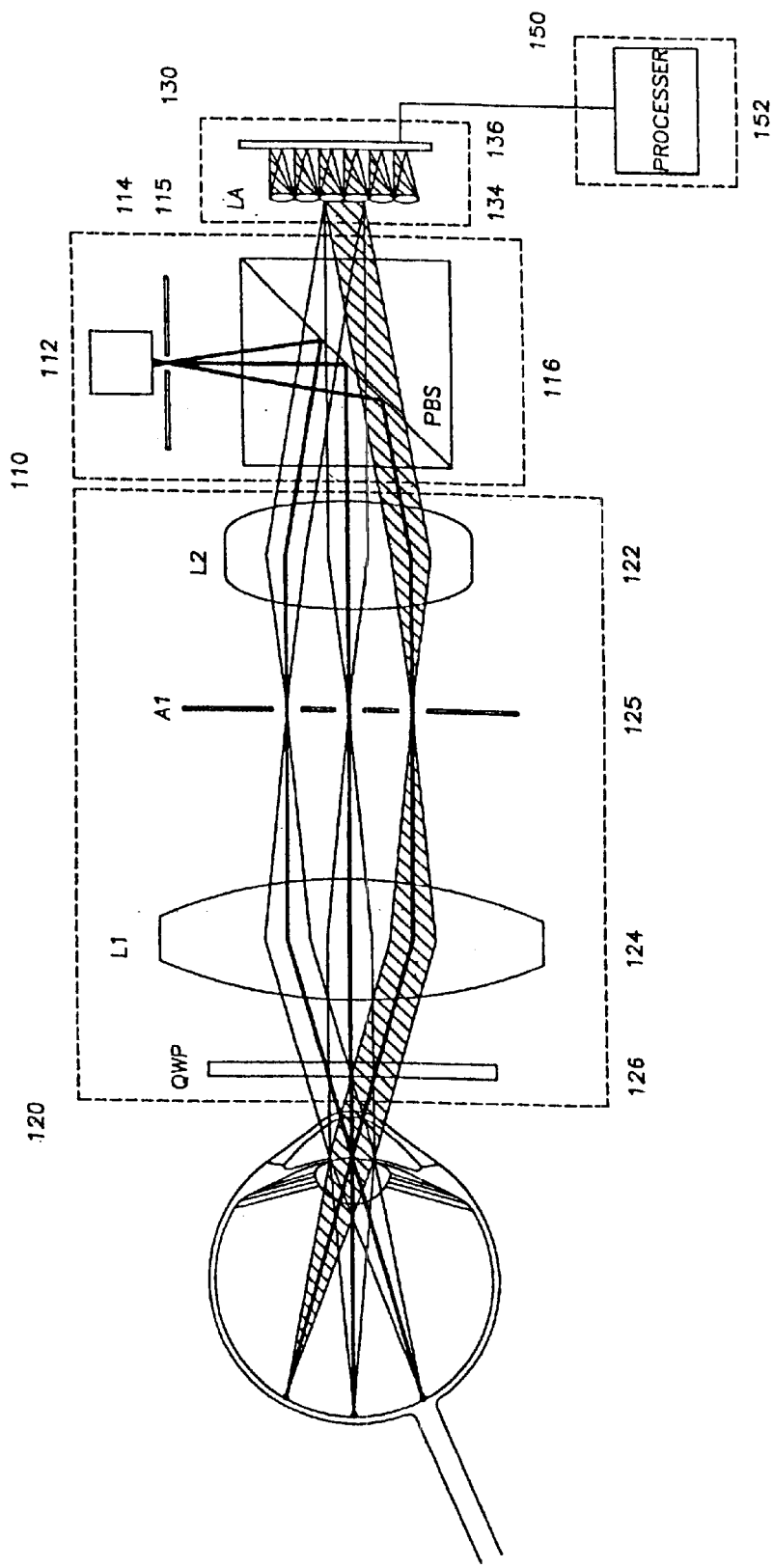
FIG. 1A shows a tomographic wavefront analysis system.

FIG. 1A shows a generalized diagram of one embodiment for a tomographic wavefront analysis system 100. In general, the tomographic wavefront analysis system 100 includes: a projection system 110 comprising a light source 112, a collimating lens 114, an aperture 115, and a polarizing beam splitter 116; an optical imaging system 120 comprising lenses 122 and 124, aperture 125, and quarter wave plate 126; and a wavefront sensor 130 including a lenslet array 134 and a sensor (e.g., a detector array 136). The tomographic wavefront analysis system 100 also includes a data analysis system 150 including a processor 152.

The tomographic wavefront analysis system 100 measures aberrations of the optical elements that make up the eye. It projects light into the eye, pre-compensates this light for the eye's dominant aberrations, and then measures reflected and scattered light from the retina with the wavefront sensor 130 which may be, e.g., a Shack-Hartmann wavefront sensor.

Significantly, according to the present invention, the tomographic wavefront analysis system 100 is adapted to perform a combination of multiple off-axis wavefront measurements to obtain a greater depth of information than is possible from a single (typically on-axis) measurement. To this end, light is projected on the retina of the eye at several different locations or positions. The resultant light spots should be arranged so that one or more of the spots are off-axis from the line of sight determined, for example, by patient alignment with a visual target. The wavefronts produced by imaging these individual light spots through the eye and the optical system are measured independently, giving several separate wavefront sensor measurements of the eye. This information may be processed using the methods of computed automated tomography to determine the three dimensional structure of the region where all the light paths intersect.

As noted above, the tomographic wavefront analysis system 100 projects light onto the retina with an optical imaging system 120 that pre-compensates for the eye's stronger defocus and astigmatic aberrations. This increases the resolution that may be used by the wavefront sensor 130. In this configuration, it is necessary to minimize stray reflections. This may be accomplished by off-axis injection with an internal spatial filter, by the use of polarization components, or by other methods. An optical system that can inject light into the eye at a significant angle may be used. The greater the angle, the better the spatial-resolution of the measurement near the pupil. This may necessitate the use of higher numerical aperture optics than those used for direct ocular aberrometry.

It is also important to maintain the proper image distance, so that an image of the pupil is relayed to the lenslet array 134 or sensing plane of the detector array 136. With this image conjugate relationship, all of the light will be incident on the lenslet array 134 and a direct mapping may be obtained between ocular pupil and measurement plane. However, the light from each of the different spots that have been projected onto the retina will arrive from different angles at the wavefront sensor 130. Thus by the focal plane of the wavefront sensor 130, depending upon the sensor design, the spots will occupy completely different groups of pixels in the detector array 136. This can be used to separate the different measurements, as will be discussed in more detail below.

Figure 1B:
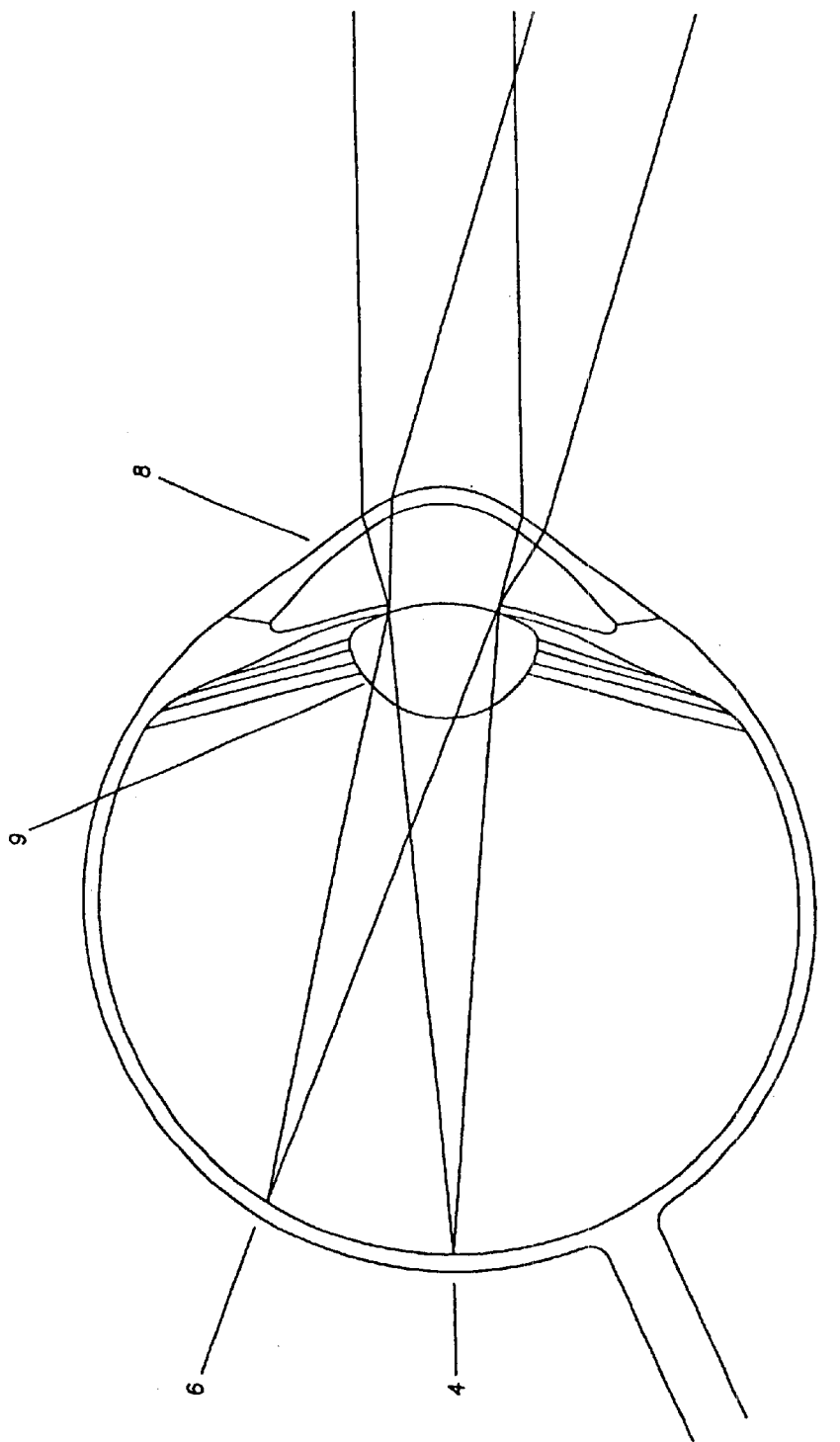
FIG. 1B shows a plurality of light spots being projected onto the retina of an eye.

In operation, as shown in FIG. 1B, an eye 2 is arranged so that its cornea 8 or pupil is conjugate to the lenslet array 134. Significantly, the projection system 110 is adapted to project a pattern of light spots onto the eye 2 at various positions 4, 6, etc., including multiple off-axis positions. The light spots may be projected simultaneously, or a pattern of spots may be sequentially created through scanning or controlling the light, as will be described in more detail below. Light scattered from these different focal spots 4, 6 traverses the crystalline lens and cornea 8 from different directions. This scattered light is collected by the optical system 120 and is analyzed by the wavefront sensor 130. While a Shack-Hartmann wavefront sensor has been shown by example, a shearing interferometer, Moiré, Hartmann or any other sensor that measures the wavefront of light can be used. The imaging system lenses 122, 124 can be adjusted to compensate for net defocus error of the eye so as to minimize the dynamic range required by the wavefront sensor 130.

In an alternative embodiment, improved resolution of structures in the eye may be obtained by varying the image distance. This can be done by leaving the eye stationary and moving the location of the wavefront sensor 130 along the optical axis. This will cause the conjugate plane of the lenslet array 134 to change to be in front of or behind the pupil of the eye. The data gathered can then be converted to three-dimensional structures of the eye by the techniques of computed automated tomography. This may be used alone or in combination with other techniques disclosed herein.

Figure 2:
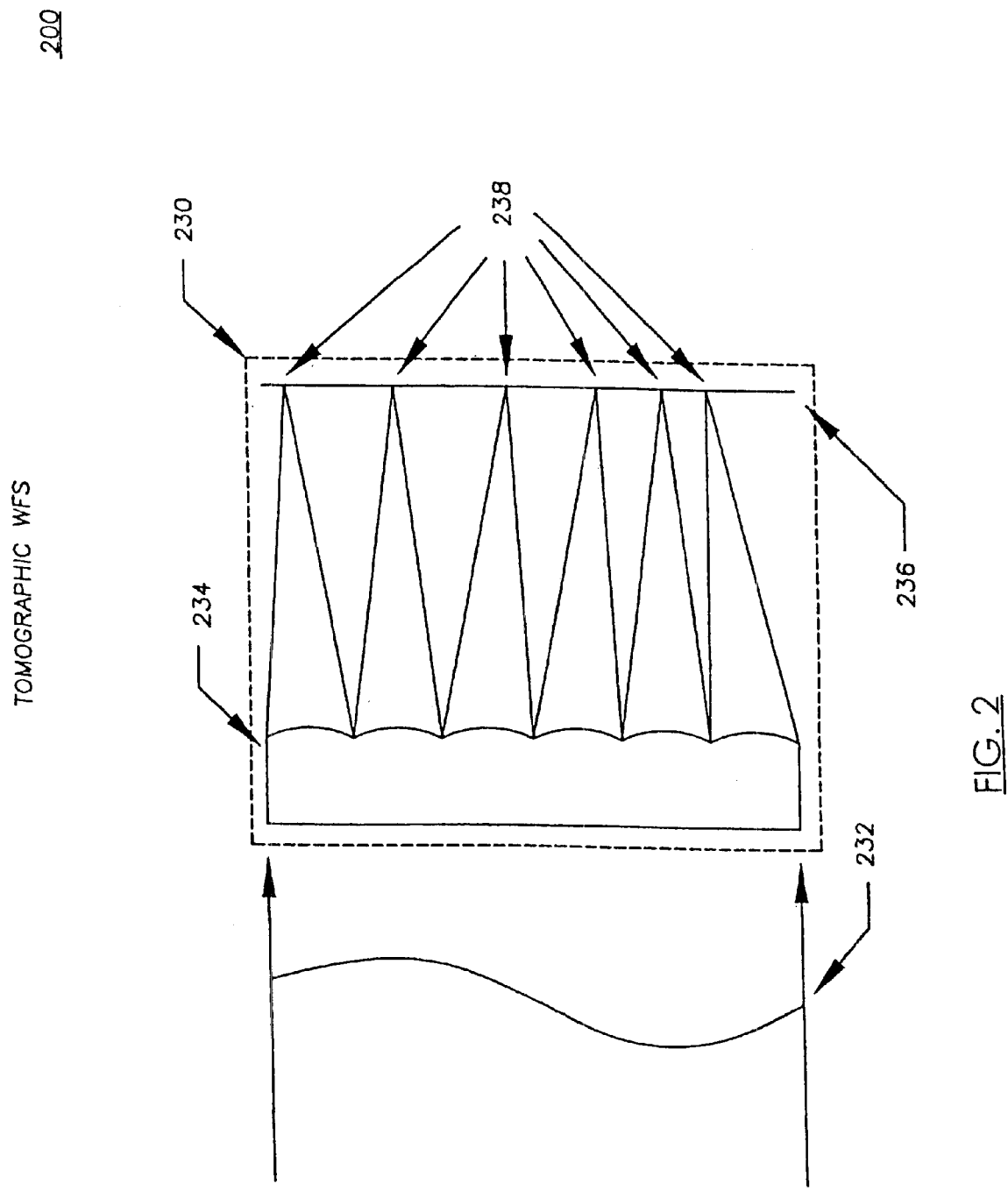
FIG. 2 shows a detailed construction of a wavefront sensor.

FIG. 2 shows a more detailed view of an embodiment of a wavefront sensor 200 that may be used in the tomographic wavefront analysis system 100. FIG. 2 shows how an incoming wavefront 232 is dissected by the lenslet array 234 to create a pattern of focal spots 238 that are detected by sensor 230. The resulting information is stored in a processor for analysis. The lenslet array 234 will create separate images on the detector array 236 for each "direction of analysis". There are a variety of ways to separate these images and determine the resulting wavefront.

Separating the various wavefront measurements so that the data can be interpreted properly is a key requirement of a system and method of measuring the aberrations of the full three-dimensional structure of the eye with a tomographic wavefront analysis system. Approaches to meeting this requirement can be divided into two general categories: (1) sequential systems/methods, and (2) simultaneous systems/methods. Each of these methods has different advantages and disadvantages.

With the simultaneous methods, it is possible to make temporally resolved measurements. This prevents an error from being generated in the measurement resulting from any movement of the eye, or changes in the medium or alignment, between measurements. However, the need for separating the various simultaneously produced images can result in a lower overall dynamic range for the system. In addition, a relatively fixed number of angular measurements are possible.

On the other hand, with sequential measurement methods, it is possible to utilize the full dynamic range of the wavefront sensor for each measurement. In addition, the number of points to be analyzed can be completely arbitrary. However, the light scanning system adds complexity (e.g., moving parts in some cases) and may be subject to changes in the medium or alignment between measurements, especially if the eye moves significantly during the measurements.

Sequential and simultaneous systems and methods, and preferred embodiments thereof, will hereafter be discussed in more detail.

Sequential Systems & Methods.

When sequential measurement is employed, light ray bundles arrive at an intermediate focal plane as separated bundles of light. This plane is conjugate to the spots projected on the retina. A mask placed at this intermediate plane can be used to separate and discriminate the various measurements. The mask can consist of a pattern of transparent regions or holes arranged in an appropriate pattern. The data can be acquired sequentially by allowing only light to pass through the desired hole. This can be controlled using one of several means. In one embodiment, a light valve, such as a liquid crystal device or other light modulation device with the appropriate pattern, is inserted at the focal plane. This light valve is sequentially operated with the proper timing to let light through at the appropriate point in the measurement sequence. Alternatively, a disk with an appropriate pattern of holes can be inserted at the intermediate focal plane. This disk is adjusted so that only one hole allows light through in any given position.

Figure 3:
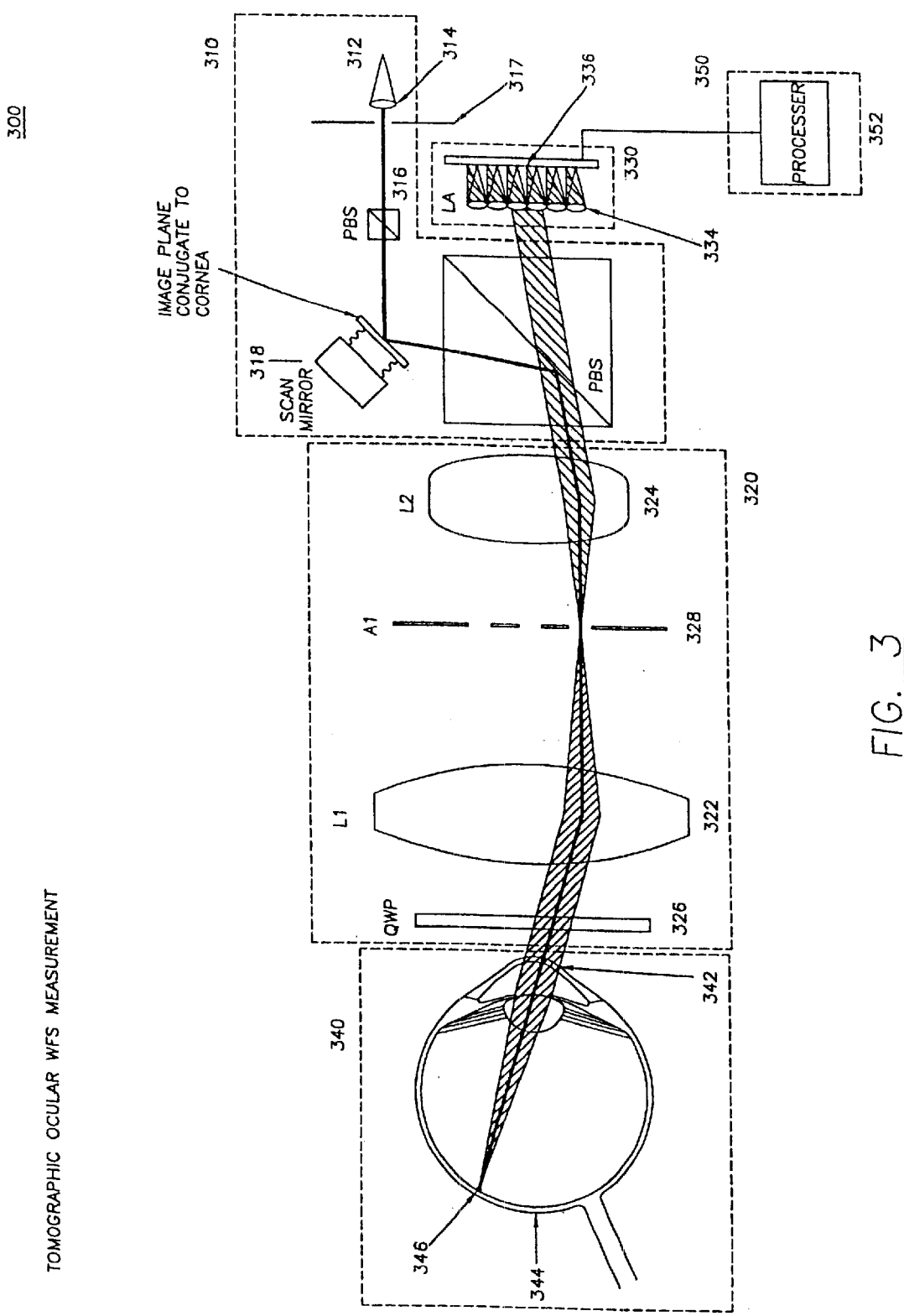
FIG. 3 shows an embodiment of a sequential-measurement tomographic wavefront analysis system.

FIG. 3 illustrates relevant portions of a sequential-measurement tomographic wavefront analysis system 300 that includes a scanning light projection system 310. The system 300 also includes an optical imaging system 320, a wavefront sensor 330, and a data analysis system 350 including a processor 352 in similarity to FIG. 1.

In the system 300, a lens 314 collimates light from a light source 312 (e.g., a laser diode or super-luminescent-diode (SLD)). The collimated light is polarized through a polarizing beam splitter 316. At an image plane that, through the optical imaging system 320, is conjugate the corneal plane, a scanning mirror 318 is used to direct the injected light beam to desired locations as a function of time. Alternatively, the scanning mirror 318 may be placed at different points in the optical imaging system 320 as required, with appropriate optics to image it to the correct conjugate plane. This scanning mirror 318 is dynamically adjusted to project focal spots at a number of different angles over a predetermined time period. With modem scanning mirrors, a very rapid set of measurements can be obtained. The measurements are synchronized to the acquisition of the wavefront sensor 330. For example, thirty measurements can readily be obtained in one second even using low cost, off-the-shelf cameras in the wavefront sensor 336.

FIG. 3, an aperture plate 328 is placed at the intermediate focal plane conjugate to the spots projected on the retina. The number of apertures in the plate 328 limits the number of different angles that can be acquired. Thus, even though the scan mirror 318 could be positioned arbitrarily to a large number of candidate positions, in practice the number of measurements is limited by the construction of the intermediate aperture plate 328. One solution to this problem has been mentioned earlier whereby the aperture plate 328 is replaced by a programmable element such as a light valve (e.g., a liquid crystal device) or other type of movable or variable aperture. While this increases the flexibility of the angular measurements, it also increases the complexity of the system.

Figure 7:
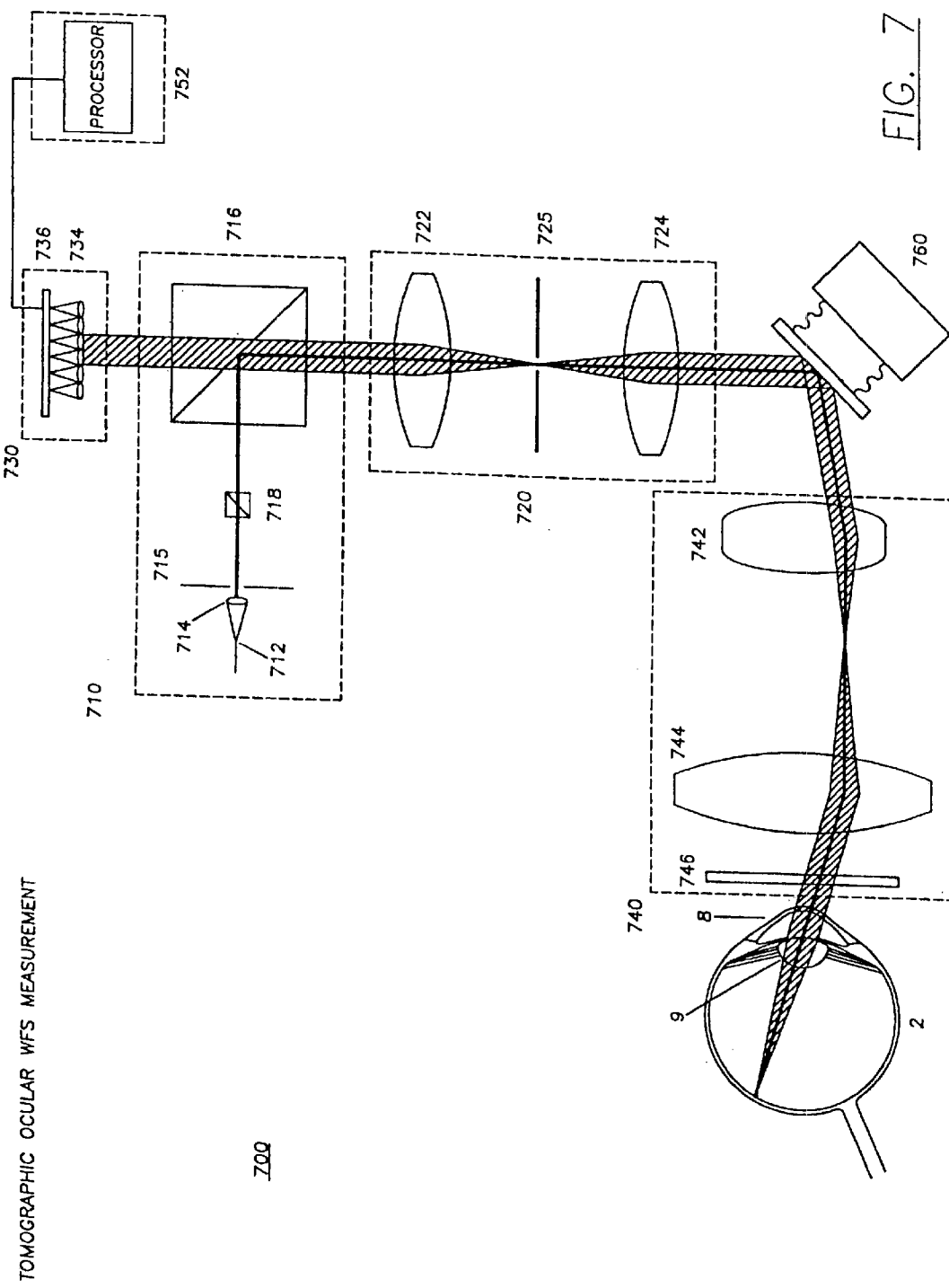
FIG. 7 shows an alternative embodiment of a sequential-measurement tomographic wavefront analysis system.

FIG. 7 is an alternative embodiment that avoids these problems without significant increase in complexity. In this case, a second relay telescope 742, 744 is added between the scanning mirror 760 and the eye 2 to facilitate acquisition of a larger number of angular measurements. Since there is no aperture plate at the intermediate plane for this second telescope 742, 744, there is no limitation on the number of scan positions. This also has the advantage that all of the pre-correction components 720 are independent from the scan components 740. This simplifies the construction of the instrument by separating the functions. The range-limiting aperture is still used at position 725, but consists of a single fixed aperture.

A detailed description of this embodiment is as follows. The projection system 710 includes a single light source 712

(which may be a laser diode, light emitting diode, or super-luminescent diode) collimated with a lens 715 and filtered with an aperture 715. The light from the projection system 710 is injected through polarizer 718 into the polarizing beam splitting cube 716. The polarizing beam splitting cube 716 reflects the s-polarized light into the optical system 720, which comprises the lenses 722 and 724 and the range-limiting aperture 725. The lenses 722 and 724 may be moved relative to one another to pre-correct both the injected and return light for the focus aberrations of the eye 2. The light is incident on the scan mirror 760, which is located at the image plane of optical system 740 conjugate to the eye 2. The scan mirror 760 is adjusted dynamically to inject and receive the light from many different angles from the eye. Since there are no apertures between the injection lenses 742 and 744, the scan mirror 760 can be used to sample a large number of points. This can be accomplished through synchronizing the scan mirror 760 to the camera acquisition. In addition, it may be desirable to use a pulsed light source 712 so that discrete locations of the signal may be recorded. The quarter wave plate 746 converts the linearly polarized light into circularly polarized light before injection into the eye 2. After scattering from the retina surface, the light is collected by the crystalline lens 9 and the cornea 8 and imaging system 740. This light will have orthogonal polarization to the injected beam. It will also return in a path parallel and collinear with the injected beam. The scan mirror 760 will then re-orient this light to be exactly aligned with the optical axis of the wavefront sensor 730, where it will be collected by optical system 720 and re-imaged onto the wavefront sensor 730. In this configuration, the wavefront sensor 730 always receives nearly collimated light that is well aligned with the optical system, since all the light that is incident on the lenslet array 734 must have passed through the range limiting aperture 725, and thus can not be deviated by more than the dynamic range of the wavefront sensor 730. The position of the scan mirror 760 for each measurement angle is recorded and used to determine the angle of the measurement. This is used in the data analysis by data analysis system 750 including a processor 752, to determine the internal structure of the eye.

Simultaneous Systems & Methods.

To simultaneously record the various required images, some form of angle-dependent encoding is needed. Each focal spot on the back of the eye must be encoded with information regarding its location. This can be done in several ways.

In one embodiment, position encoding may be employed. In that case, a wavefront sensor that spatially separates the light from the various fields at widely different angles is employed. In one embodiment, the wavefront sensor includes a lenslet array that is "smaller" than the detector array. Such encoding may be performed using a camera (e.g. a KODAK Megapixel or SMD 1M15), with having more total pixels than the number of lenses in the lenslet array, so that each lenslet would map onto a larger number of pixels. Thus, the measurements do not overlap, allowing simultaneous acquisition. This allows the sub-areas-of-interest needed for position encoding.

Alternatively, wavelength encoding is employed. By simultaneously projecting a slightly different color of light onto each location of the eye being measured, each spot is "color-coded". In this case, a color wavefront sensor is employed for straightforward decoding of the signal. Accordingly, the various spots are allowed to overlap from the different fields.

Figure 4:
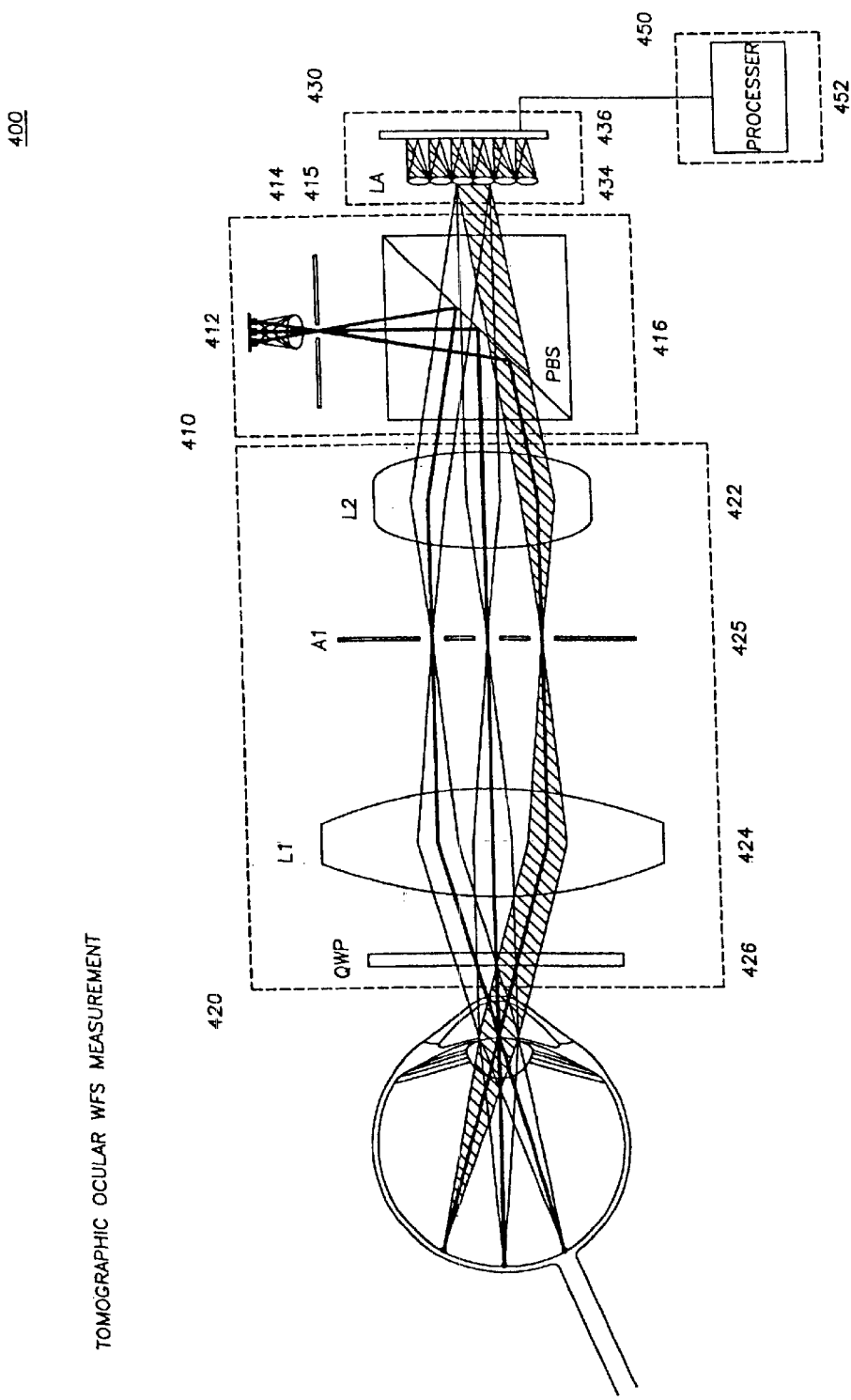
FIG. 4 shows an embodiment of a simultaneous-measurement tomographic wavefront analysis system.

FIG. 4 illustrates relevant portions of a simultaneous-measurement tomographic wavefront analysis system 400 that includes a light projection system 410 for simultaneously projecting a pattern of focal spots onto the retina of the eye. The system 400 also includes an optical imaging system 420, a wavefront sensor 430, a data analysis system 450 including a processor 452 that are each functionally similar to the corresponding components shown in FIG. 1.

Figure 5:
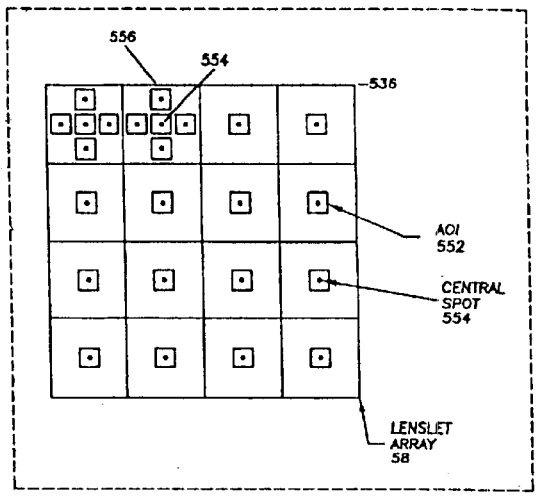
FIGS. 5A–5D illustrate relevant portions of a system and method for simultaneously analyzing wavefronts measured at different angles of analysis.
Figure 5:
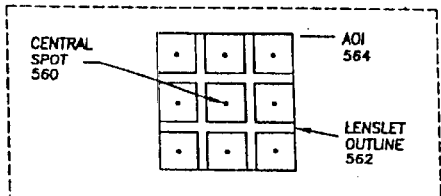
Figure 5:
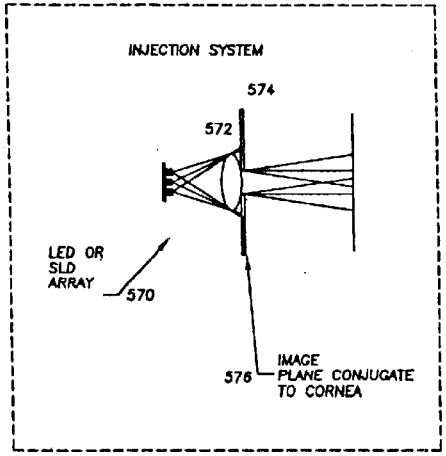
Figure 5:
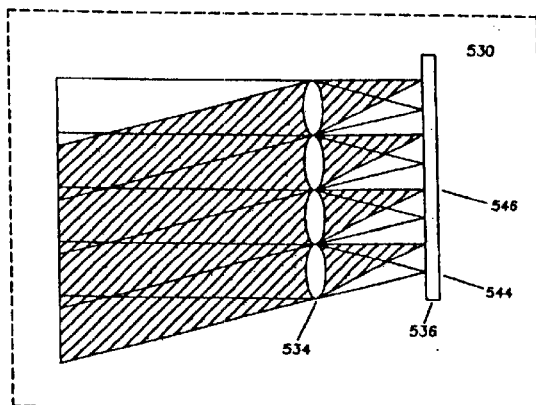

In the system 400, a number of point light sources 412 are provided by, for example an array of SLDs, light emitting diodes (LEDs), or even holes in a back illuminated plate (also shown in FIG. 5C). The light sources 412 are imaged through a single lens 414 and an aperture grid 415. The lens 414 transforms the linear position differences of the light sources 412 into a set of collimated beams at different angles. The optical imaging system 420 is used to image the different light beams at different angles to different spots on the retina of the eye.

FIGS. 5A–5C illustrate relevant portions of a system and method for simultaneously analyzing wavefronts measured at different angles of analysis. In this configuration a number of spots are simultaneously projected onto the retina at different positions using a system and method, e.g. the system 400 shown in FIG. 4 above. FIG. 5A shows the pattern of focal spots on the detector array 536. In this pattern, there is a central spot 554 and one or more off-axis spots 556. These focal spots are spatially isolated due to the differences in the angle-of-arrival. FIG. 5D shows a detailed cross-section view of a lenslet array 534 for a Shack-Hartmann wavefront sensor 530, where light from all of the different views are incident upon the lenslet array 534 and thus focused onto a detector array 536. The different angles-of-arrival result in spatially separated spots 544 and 546. By assigning each of these spots to its own Area Of Interest (AOI) 552, the centroid location can be determined within the AOI. A reference set of wavefronts can be recorded with the same system to establish the location of these AOIs and to establish the appropriate mapping. With this arrangement, it is convenient to analyze up to nine focal spots per lenslet as shown in FIG. 5B. In this case the lenslet aperture 562 is arranged with the focal spots on the boundary and corners. Each focal spot 560 has the same size AOI 564. Adjacent lenslets have a similar pattern. This type of system may require the use of a large format camera to achieve the same resolution obtainable from a single focal spot. FIG. 5C shows how an array of SLDs or LEDs 570 can be used to create a plurality of beams at different angles. This is accomplished by collimating the emitted light with the lens 572 and limiting the beam size with the aperture 574.

Figure 6:
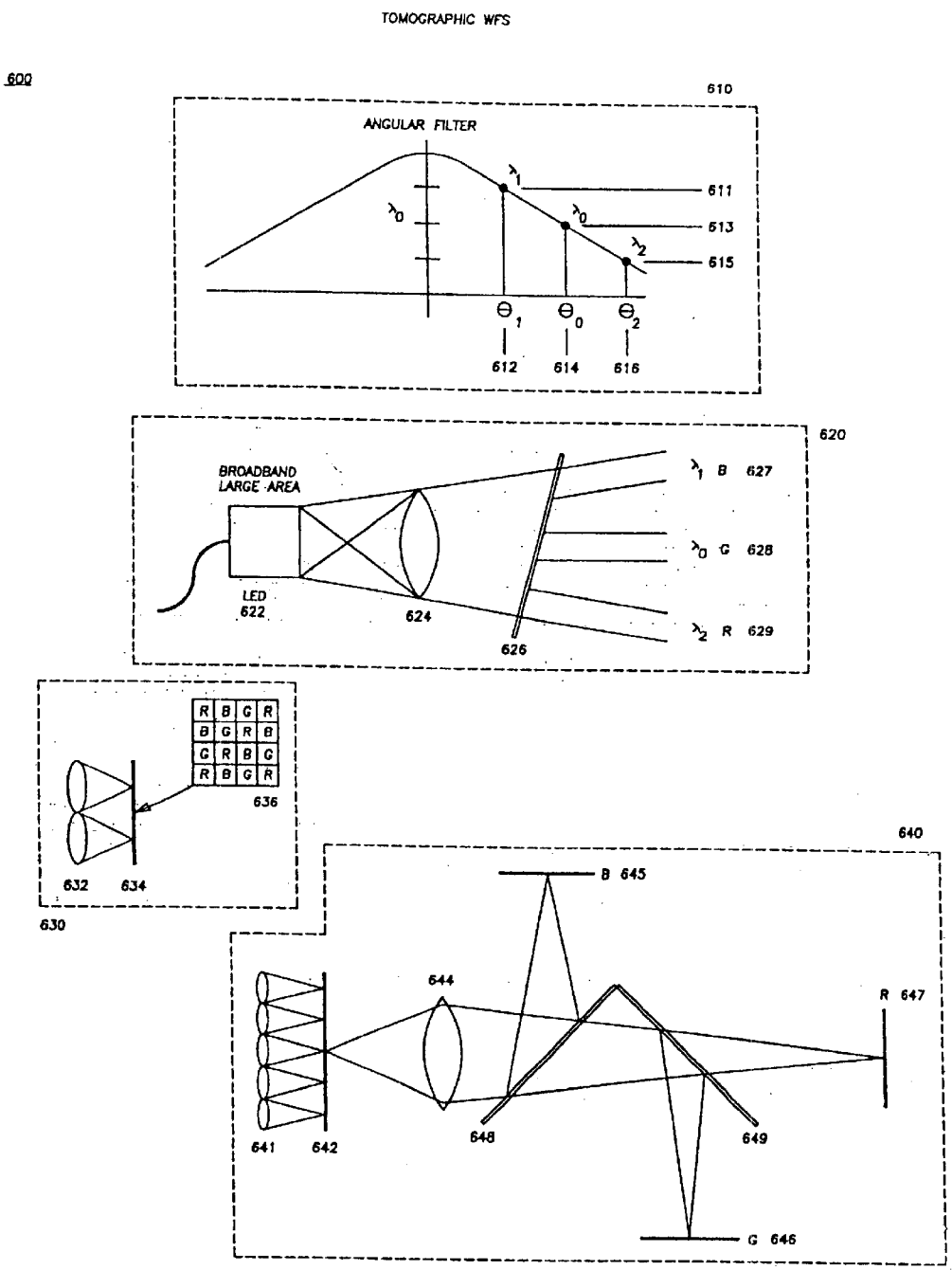
FIG. 6 shows a system for spectrally separating focal spots to be projected onto an eye and detecting these spots with a color wavefront sensor.

FIG. 6 illustrates a system and method for spectrally coding the focal spots projected onto the retina and spectrally separating the scattered light received back from the focal spots. To this end, each of the focal spots is coded by using light of a slightly different wavelength, $\lambda$. This coding can be achieved with an angular-tuned filter 626, or by using different color SLDs or LEDs. A three-color CCD camera 640, for example, is used to spectrally separate the images onto three separate CCD detector planes 645, 646 and 647. This allows high dynamic range, high-resolution wavefront measurements to be made with a simple optical system. However, such a system and method is limited in practice to examining a few, e.g., three angles.

With a pair of continuously variable filters, it is possible to examine a much wider frequency range. Using LCD technology, it is possible to build electrically controlled optical filters. A fixed pattern of different color focal spots is projected onto the eye, and the images sequentially recorded with different settings of the electronic filter. This has the advantage of no moving parts, but requires sequential acquisition of the data, similar to the scanning systems discussed above.

The details of a spectral separation system and method will now be presented in more detail. An angularly tuned filter 626 can be constructed using the principle of narrow band interference coatings. The filter can be either reflective or transmissive, depending upon the design of the coatings. A filter of this type will exhibit the properties described in FIG. 6. In this case, varying the angle of the filter will vary the wavelength of light that it transmits or reflects. By choosing a nominal design point 614 with the filter 626 at a tilted position, the wavelength can be adjusted both up 611 and down 615 from the center wavelength 613 at the corresponding angles. Thus, a broad-band source 622 (at least broader than the spread in wavelengths $\lambda_1$ 611 to $\lambda_2$ 615), can be used in combination with the filter 626 to create light that is coded angularly with wavelength according to 620. In this case, a large LED 622 is approximately collimated with lens 624. The large area of the source 622 leads to a range of angles after collimation through the lens 624. After passing through the filter 626 described previously, the light at a given angle will be coded by wavelength. Thus is provided a means for associating light at a particular angle with a particular wavelength.

This light source 620 can then be used, instead of the source 412, in conjunction with the tomographic wavefront sensor 400 for simultaneous recording and detection of the wavefront at different probe angles through the optical system. After passing through the optical system 420, the eye 2, and returning to the wavefront sensor 430, the light from the different angles will be incident on the lenslet array 434 and create focal spots on the detector array 436. These spots may, in general, overlap. The spots are detected and separated by use of the color wavefront sensor 630 or 640.

In one embodiment, the color wavefront sensor 630 consists of a mosaic focal plane detector with color filters arranged over the various pixels. A refractive lenslet array 632 is used in front of the detector mosaic 636 to create the focal spots in a manner that is not dependent upon the wavelength of the incident light. Since the mosaic of detector elements 636 includes samples at multiple different colors, reading only those pixels that have a coding for a particular wavelength (e.g. "B") will result in reading out the information pertaining only to the particular color (e.g. "B"), even though spots created by a different color incident light are also present and may even overlap. This method of recording the position of focal spots that are spectrally coded is very simple and robust, but is limited to a few colors in order to maximize the resolution of the spot decimation and position finding. Commercial mosaic focal plane arrays are available that have red, green and blue coatings (RGB) and are in common use as color imaging sensors. However, for the tomographic wavefront sensor 100, it may be more useful to build a special color wavefront sensor 630 with a different spectral range. For example the pixels labeled RGB may consist of filters with 850, 830 and 810 nm respectively.

An alternative embodiment for the color wavefront sensor is the 3-CCD camera system shown in 640. In this embodiment, the lenslet array 641 creates focal spots at intermediate image plane 642. These spots may overlap, but are the result of the color coding scheme 620 and are thus spectrally separate. The relay imaging lens 644 is used to relay the image of the intermediate image plane to detector planes 645, 646, and 647. At each of these planes a detector array (e.g. a CCD array) is located. The spectral filters 648 and 649 are used to spectrally isolate the wavelengths that can be transmitted to each of the respective detector planes. Thus the full image of the focal spot pattern at the intermediate image plate 642 is present at each detector plane 645, 646 and 647, but spectrally isolated according to the desired color-coding.

Color 3-CCD imaging sensors are available commercially with spectral coatings for red, green and blue wavelengths. For use in the tomographic wavefront analysis system 100, a different set of filters may be chosen with wavelengths appropriate for the eye measurement (e.g. 850, 830 and 810 nm).

A larger number of wavelengths may be used to provide more than three angular samples with the tomographic wavefront analysis system 100. These may be arranged in combination with the spatial separation techniques 400 to create a larger grid of measurement angles. For example, if three colors (e.g. 850, 830 and 810 nm) are spectrally isolated, then a pattern arranged in both the x-direction and y-direction can be arranged by using a pair of filters 626 arranged in orthogonal directions. This will allow up to nine different angles to be sampled while allowing the spots to overlap somewhat and taking advantage of all other features of the invention.

Other arrangements are possible, and may be readily identified by those skilled in the art.

Figure 9:
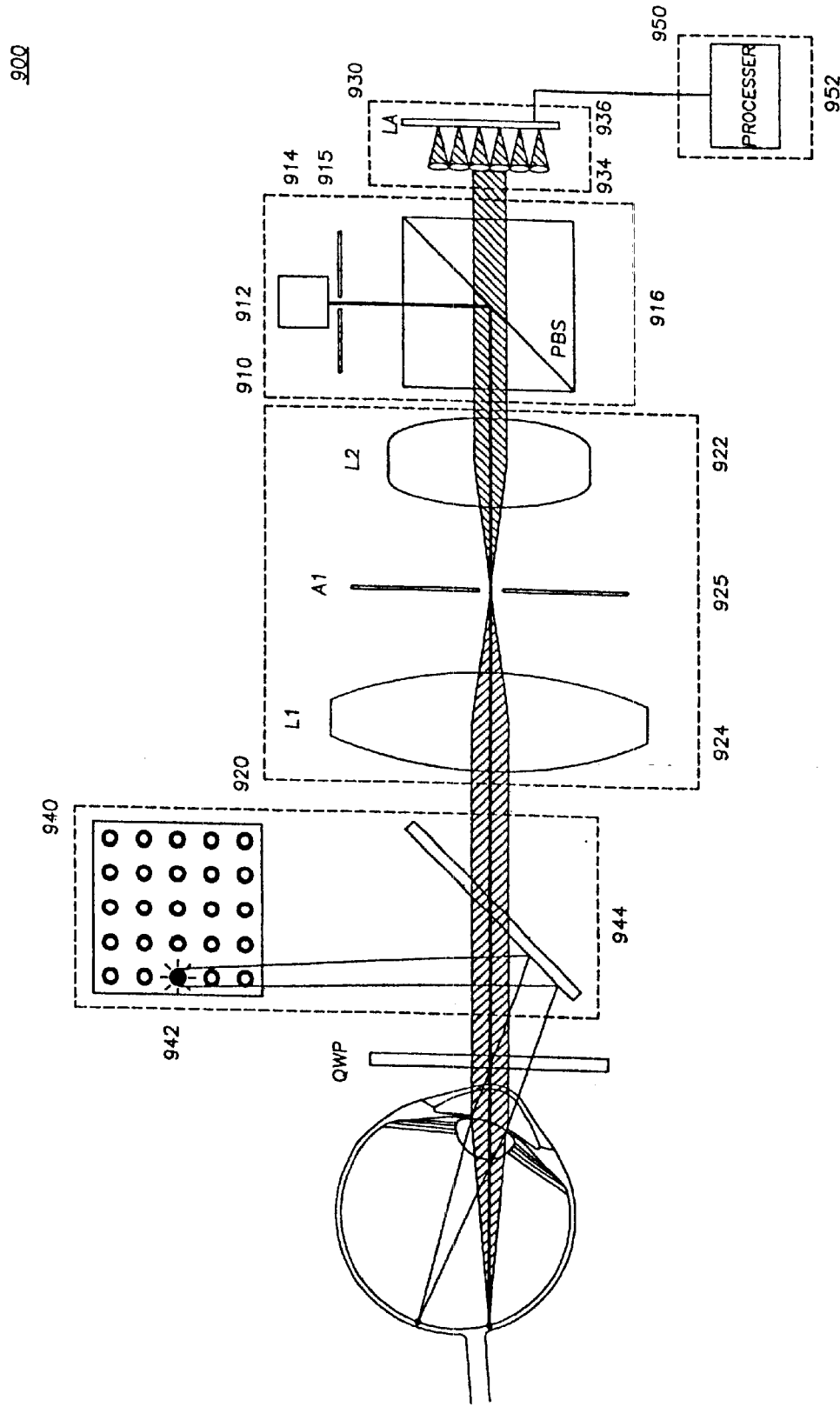
FIG. 9 shows a method for measuring the eye at different angles by changing a target fixation point.

For example, as described above, the primary requirement of the tomographic wavefront sensor system is the ability to make measurements of the optical system, e.g. the eye, at different angles. While FIGS. 1–7 depict different arrangements for objectively and mechanically making simultaneous or sequential measurements of the optical wavefront aberration from different angle measurements, it is also possible to acquire these measurements by moving the object under test. For the case of the human eye this can be accomplished by using an instrument similar to that described in the WFS.006 Application, with the exception of a change in the target. As depicted in FIG. 9. The instrument in the WFS.006 Application includes an internal target system 940 that is used for patient fixation and to control patient accommodation. To make measurements of the eye at different angles, the target 942 in the target system 940 can be changed to force the eye to focus on different positions. Instead of focusing only on an axis that is directly aligned with the optical system of the measuring instrument, the target can be arranged with a number of off-axis locations. This can be achieved either by physically moving the target 942, or by providing an electronic or other means for repositioning the apparent position of the target center. As an example, a grid of light emitting diodes that could be individually controlled could be used as a target. In this case the individual LED corresponding to the desired measurement would be illuminated, then the corresponding wavefront recorded, then the next LED corresponding to the next desired measurement location illuminated, and so on successively until all the desired measurements have been made. This provides the same measurements, with a similar number of different angular positions as the other methods described above. However, while simple, this method has the disadvantage that the separate measurements are made at times that are widely separated. Thus the average performance of the eye under test would be measured. This, in many cases, is adequate.

Data Analysis.

An objective of the previously described methods and systems was to develop a set of measurement data of the optical system from a number of different angles. With the measurements being performed simultaneously, or nearly simultaneously, the measured data can be used together to determine many of the details of the internal optical system. This is what is called tomographic reconstruction. As shown in FIG. 1, the data gathered by the wavefront sensor 130 is provided to a data analysis system 150 including a processor 152 and memory. As described in more detail below, the data analysis system 150 performs a tomographic reconstruction of the optical system (e.g., the eye) by processing the measured data according to one or more aspects of the invention.

An example of measuring the same optical system at several different angles is shown in FIGS. 8A–D.

Figure 8:
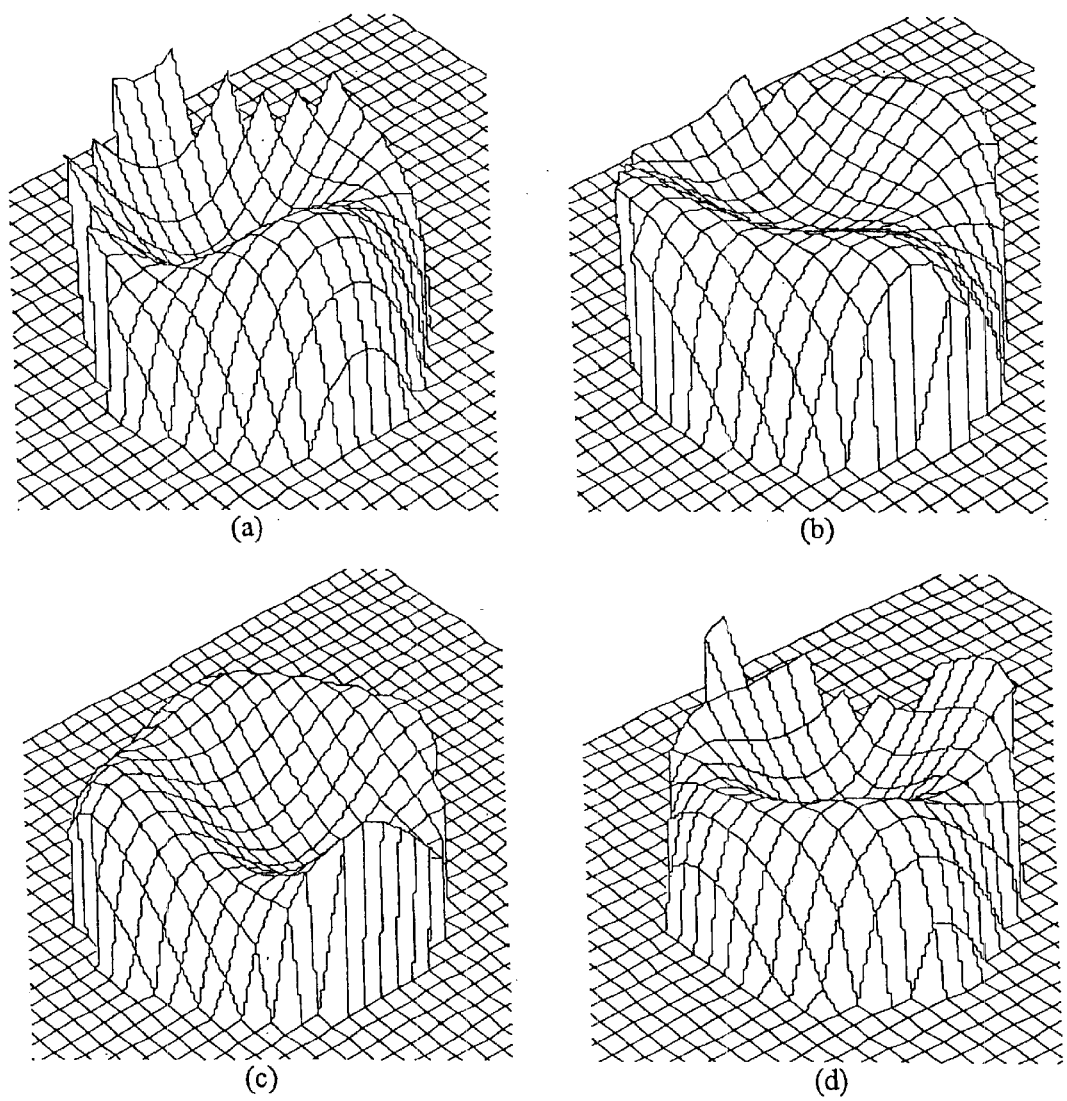
FIGS. 8A–D show four different wavefront maps from the same eye that have been measured and analyzed with an ophthalmic wavefront analysis system.

FIGS. 8A–D show four different wavefront maps from the same eye that have been measured and analyzed with the ophthalmic wavefront analysis system described in the WFS.006 Application. In FIG. 8*a*, the on-axis aberrations are shown. FIGS. 8B–D are off-axis measurements of the same eye, where the measurements were acquired with the eye approximately 15 degrees left, 15 degrees up and 15 degrees down, successively. The low order aberrations were removed from wavefronts that are presented in FIGS. 8A–D for clarity. It is clear from examining these images that the angular position of the eye has a big influence on the resulting aberrations. By combining the information contained in a number of such measurements the internal structure can be determined.

In a classic tomographic reconstruction, such as in a computer automated tomography (CAT) scan or magnetic resonance imaging (MRI) procedure, a number of data sets are acquired from many different angles through the system. In this case, the 3D structure being measured is constructed from a number of different discrete measurements. Fourier transform techniques can then be used to reconstruct the internal structure. This can also be used in the tomographic wavefront sensor. In this case the wavefront can be sampled at the resolution of the lenslet array (or interpolated if appropriate to provide higher resolution), and then the different fields can be fed into the tomographic reconstruction algorithm.

An alternative method can also be used for optical systems, such as the eye, where some knowledge of the internal structure is known in advance ("a-priori"). The eye, for example, has several external and internal surfaces where there are differences in the index of refraction. These include the cornea anterior and posterior surface, the anterior chamber, the crystalline lens (posterior and anterior surface) the vitreous and the retina. While the exact location, separation, curvature, and shape of these various elements is not known, there are a fairly limited number of elements that are needed to describe the internal structure.

The internal structure of the lens in the eye is known to have an index of refraction that varies with the radial position from the center of the lens and this radial dependence may also be measured by the tomographic analysis.

Since Zernike polynomials are commonly used to describe the wavefront, it is natural to use these same polynomials to describe the shape of the various internal components. However, these are convenient mathematical constructs only, and any other set of polynomials or mathematical descriptors can be used.

The various surfaces are described in terms of the following:

| | |
|---|---|
| Sca | Anterior Surface of the cornea |
| Scp | Posterior surface of cornea |
| tc | Corneal center thickness |
| tac | Anterior chamber center thickness |

-continued

| | |
|---|---|
| Sla | Anterior surface of the crystalline lens |
| Slp | Posterior surface of the crystalline lens |
| tl | Crystalline lens center thickness |

The various surfaces can also be described in terms of a few additional constants. These include the radius of curvature, conic constant and coefficients that represent small deviations from these shapes. For example, the surfaces can be represented by:

$$S(x, y) = \frac{C_x x^2 + C_y y^2}{1 + \sqrt{1 - (1+k_x)(C_x^2 x^2) - (1+k_y)(C_y^2 y^2)}} + \sum_{k=6}^{N} a_k Z_k(x, y)$$

where:

$C_x$ and $C_y$ are constants defining the radius of curvatures in the x and y directions;

$k_x$ and $k_y$ are conic constants in the x and y directions;

$Z_k$ define a set of polynomials; and $a_k$ are polynomial coefficients.

This description of the surfaces includes a general anarnorphic conic surface shape and arbitrary deviation from the pure conic shape. To the fourth order, this surface requires 13 parameters to be completely described. Each of the four surfaces, Sca, Scp, Sla and Slp can be expanded in this way. In addition, each of these surfaces may have principle axes that are rotated relative to the reference frame, yielding an additional parameter for each surface. Thus each surface (to the fourth order) would need 14 parameters. Including the various center thicknesses, this yields a total of 60 parameters to completely describe the eye, including the internal structure. These parameters may conveniently be collected into a single list, $b_k$, where k=(1, 60). Knowledge of these parameters would give the total transmitted wavefront error, the corneal surface curvature, shape and thickness, the internal lens shape, thickness and wavefront error. The data can be analyzed from many different standpoints. For example, the combined on-axis corneal topography and wavefront measurement can be readily generated. A corneal thickness map (pachymmetry) or cornea surface curvature can be readily determined from the data. In short, this provides all of the information needed for complete analysis of the eye for diagnosis, pathology, surgery planning and many other applications.

Each of the measurements at the various angles provides information about the rays that are collected through that particular angle. These describe the best-fit expansion of the wavefront in terms of Zernike or other polynomials. However, for a high-resolution instrument (see, e.g., the WFS.006 Application) this may be the result of fitting over 800 individual slope measurements to the data. Given that it may be desirable to probe the ocular system from a number of different angles (3 to 25), there are a very large number of individual measurements that can be used to determine the internal structure. The system is significantly over-determined.

The analysis proceeds by forming a metric, which describes the net optical path difference (OPD) between the parameterized surface and the measured data. Thus, for each angle that is probed by the tomographic wavefront system α, the net OPD is determined by a ray trace through the optical system with the parameters that describe the surfaces $b_k$ consisting of a list of the previous surface parameters. This is compared to the measured optical path difference ($OPD_m$) for that angle, and summed over all angles and all points in each field:

$$\chi^2 = \sum_\alpha \sum_{x,y} [OPD(b_k, \alpha, x, y) - OPD_{m,\alpha}(x, y)]^2 \qquad 5$$

This now allows a normal least-squares solution for the parameters $b_k$ through minimization of $\chi^2$ with respect to the parameters $b_k$. A number of methods exist for this solution, including Gauss-Seidel solution, singular value decomposition or iterative least-squares. If some of these surfaces are known from other measurements, such as a corneal topography measurement (e.g., Sca and Scp are known), then this information can be used to improve the accuracy of determining the other parameters.

The advantage of this type of technique over the Fourier transform tomographic reconstruction methods is that the resolution of the Shack-Hartmann wavefront sensor is inherently dissimilar in the spatial directions (x, y) versus the ordinal direction (z). The lenslet array (or pixel size for other wavefront measurement methods) determines the spatial resolution, whereas the wavefront resolution (the minimum wavefront that can be accurately determined) is determined by detector and lenslet characteristics, algorithms and other effects. Typically the spatial resolution may be 200–300 $\mu$m, whereas the wavefront resolution may be less than 0.1 $\mu$m. Thus the Fourier transform method, while applicable to this application, may yield results that are at the lenslet resolution (200–300$\mu$m). This may not be adequate for some applications.

The least-squares fit method should result in measurements that are accurate to the sub-micron level except where the various angles do not overlap. This non-overlapping region is conveniently handled by the polynomial representation, since it includes the best definition for the various surfaces even for regions of only partial overlap.

When a person focuses their eyes at different distances, the internal shape of the lens inside the eye changes while the other structures in the eye change very little. In one embodiment, a target is incorporated that is presented at different distances for the patient to focus on. Then the tomographic measurement is done with the eye focused at different distances. The mathematical algorithms are adjusted to keep some of the parameters of the three-dimensional structure fixed, while allowing the shape and thickness of the lens to vary to best fit the measured data. This technique allows for increased resolution in the measurement of the structures in the eye.

In some cases, symmetry or other mathematical effect may limit the accuracy of the terms that can be derived. For structures that are far removed from the pupil of the optical system, the overlap of the various probe angles may be reduced. Thus the full aberrations may have a limited pupil over which they can be determined. These limitations depend upon the details of the particular embodiment and are not limitations of the invention itself.

While preferred embodiments are disclosed herein, many variations are possible which remain within the concept and scope of the invention. Such variations would become clear to one of ordinary skill in the art after inspection of the specification, drawings and claims herein. The invention therefore is not to be restricted except within the spirit and scope of the appended claims.

What is claimed is:

1. A tomographic wavefront analysis system, comprising:
   a projection system projecting a plurality of light beams, the projection system comprising,
   a light source simultaneously producing a plurality of light beams,
   a collimating lens collimating the plurality of light beams,
   an aperture grid passing therethrough the plurality of collimated light beams;
   a polarizing beam splitter receiving and polarizing the plurality of collimated light beams; and
   an optical imaging system receiving the polarized collimated light beams and simultaneously providing the polarized collimated light beams onto a plurality of different locations in an eye; and
   a wavefront sensor simultaneously receiving scattered light from each of the locations, the wavefront sensor including
   a lenslet array, receiving and focusing the scattered light, and
   a detector array detecting the focused scattered light.

2. The system of claim 1, wherein the optical imaging system comprises:
   a pair of lenses disposed in an optical path between the scanning mirror and the eye; and
   a quarterwave plated disposed in an optical path between the pair of lenses and the eye.

3. The system of claim 1, wherein the light source produces a plurality of light beams each having substantially a same wavelength.

4. The system of claim 3, wherein the lenslet array comprises a first number of lenslets and the detector array comprises a second number of pixels, and wherein the second number is substantially greater than the first number.

5. The system of claim 1, wherein the light source produces a plurality of light beams each having a corresponding different wavelength.

6. The system of claim 5, wherein the detector array comprises a mosaic pattern of color-coded pixels, each color-coded pixel substantially detecting only light corresponding to one of the different wavelengths.

7. The system of claim 5, wherein the wavefront sensor further comprises second and third detector arrays, each of the detector arrays being color-coded to substantially detect only light corresponding to one of the different wavelengths.

8. The system of claim 7, wherein the wavefront sensor further comprises at least one spectral filter disposed in an optical path between the lenslet array and the detector arrays, the spectral filter spectrally filtering the focused scattered light provided to the detector arrays.

9. The system of claim 1, further comprising a processor receiving data from the detector array and determining therefrom a set of parameters describing surfaces of structures internal to the eye.

10. A tomographic wavefront analysis system, comprising:
    a projection system projecting a scanned, polarized, collimated light beam, the projection system comprising,
    a light source producing a light beam,
    a collimating lens collimating the light beam,
    an aperture grid passing therethrough the collimated light beam;
    a polarizing beam splitter receiving and polarizing the collimated light beam,
    a scanning mirror reflecting and scanning the light beam over a plurality of desired directions as a function of time; and
    an optical imaging system receiving the scanned, polarized, collimated light beam and directing the scanned polarized collimated light beam onto a plurality of different locations in an eye; and a wavefront sensor receiving scattered light from each of the locations, the wavefront sensor including a lenslet array, receiving and focusing the scattered light, and a detector array detecting the focused scattered light.

11. The system of claim 10, further comprising a light valve disposed in an optical path between the eye and the wavefront sensor, the light valve sequentially passing the scattered light to the wavefront sensor.

12. The system of claim 11, where the light valve is disposed at an intermediate focal plane conjugate to the locations in the eye where the light is scattered.

13. The system of claim 11, wherein the light valve comprises a liquid crystal device.

14. The system of claim 10, further comprising a disk disposed in an optical path between the eye and the wavefront sensor, the disk having a pattern of holes therein selectively passing the scattered light to the wavefront sensor.

15. The system of claim 10, wherein the optical imaging system comprises:

a pair of lenses disposed in an optical path between the scanning mirror and the eye; and a quarterwave plated disposed in an optical path between the pair of lenses and the eye.

16. The system of claim 10, further comprising a relay telescope disposed in an optical path between the light source and the scanning mirror, the relay telescope comprising first and second lenses and a plate with an aperture therein disposed between the first and second lenses.

17. The system of claim 16, wherein the optical imaging system consists of:

a pair of lenses disposed in an optical path between the scanning mirror and the eye; and a quarterwave plated disposed in an optical path between the pair of lenses and the eye.

18. The system of claim 10, wherein the scanning mirror is synchronized with detector array.

19. The system of claim 10, further comprising a processor receiving data from the detector array and determining therefrom a set of parameters describing surfaces of structures internal to the eye.

20. A tomographic wavefront analysis system, comprising:

a projection system creating a plurality of collimated light beams;

an optical imaging system receiving the plurality of collimated light beams and simultaneously providing the plurality of collimated light beams onto a plurality of different locations in an eye; and a wavefront sensor simultaneously receiving scattered light from each of the different locations.

21. The system of claim 20, wherein the optical imaging system comprises:

a pair of lenses disposed in an optical path between the projection system and the eye; and a quarterwave plated disposed in an optical path between the pair of lenses and the eye.

22. The system of claim 20, wherein the projection system produces a plurality of light beams each having substantially a same wavelength.

23. The system of claim 22, wherein the wavefront sensor comprises:

a lenslet array having a first number of lenslets receiving and focusing the scattered light; and a detector array having a second number of pixels detecting the focused scattered light, wherein the second number is substantially greater than the first number.

24. The system of claim 20, wherein the projection system produces a plurality of light beams each having a corresponding different wavelength.

25. The system of claim 24, wherein the wavefront sensor comprises:

a lenslet array receiving and focusing the scattered light; and a detector array having a mosaic pattern of color-coded pixels detecting the focused scattered light, wherein each color-coded pixel substantially detects only light corresponding to one of the different wavelengths.

26. The system of claim 24, wherein the wavefront sensor comprises a plurality of detector arrays, each of the detector arrays being color-coded to substantially detect only light corresponding to one of the different wavelengths.

27. The system of claim 26, wherein the wavefront sensor further comprises at least one spectral filter disposed in an optical path between the lenslet array and the detector arrays, the spectral filter spectrally filtering the focused scattered light provided to the detector arrays.

28. The system of claim 20, further comprising a processor receiving data from the wavefront sensor and determining therefrom a set of parameters describing surfaces of structures internal to the eye.

29. A method of measuring aberrations of a three-dimensional structure of a target optical system, comprising:

creating a plurality of collimated light beams;

simultaneously providing the plurality of collimated light beams onto a plurality of different locations in the target optical system; and simultaneously receiving scattered light from each of the different locations.

30. The method of claim 29, wherein creating a plurality of collimated light beams comprises creating a plurality of collimated light beams each having substantially a same wavelength.

31. The method of claim 29, wherein creating a plurality of collimated light beams comprises creating a plurality of collimated light beams each having a corresponding different wavelength.

32. The method of claim 29, further comprising:

detecting wavefront data from the scattered light; and processing the detected wavefront data to determine therefrom a set of parameters describing surfaces of structures internal to the target optical system.

33. The method of claim 32, wherein processing the detected wavefront data to determine therefrom a set of parameters describing surfaces of structures internal to the target optical system includes using a priori information regarding the internal structures increase an accuracy of the determined set of parameters.

34. The method of claim 29, wherein the target optical system is an eye, and further comprising:

performing a corneal topography measurement of the eye;

detecting wavefront data from the scattered light; and processing the detected wavefront data to determine therefrom a set of parameters describing surfaces of internal structures of the eye, wherein processing the detected wavefront data includes using corneal surface parameters from the corneal topography measurement to increase an accuracy of the determined set of parameters.

35. A tomographic wavefront analysis system, comprising:
   a projection system creating a light beam and scanning the light beam in a plurality of desired directions;
   an optical imaging system receiving the scanned light beam and providing the scanned light beam onto a plurality of different locations in a target optical system; and
   a wavefront sensor receiving scattered light from each of the different locations.

36. The system of claim 35, wherein the projection system includes a scanning mirror and scanning the light beam in a plurality of desired directions.

37. The system of claim 35, further comprising a light valve disposed in an optical path between the target optical system and the wavefront sensor, the light valve sequentially passing the scattered light to the wavefront sensor.

38. The system of claim 37, wherein the light valve comprises a liquid crystal device.

39. The system of claim 35, further comprising a disk disposed in an optical path between the target optical system and the wavefront sensor, the disk having a pattern of holes therein, the disk selectively passing the scattered light to the wavefront sensor.

40. The system of claim 35, further comprising a relay telescope disposed in an optical path between the projection system and the optical imaging system, the relay telescope comprising first and second lenses and a plate with an aperture therein disposed between the first and second lenses.

41. The system of claim 40, wherein the optical imaging system consists of:
   a pair of lenses disposed in an optical path between the scanning mirror and the target optical system; and
   a quarterwave plated disposed in an optical path between the pair of lenses and the target optical system.

42. The system of claim 35, further comprising a processor receiving data from the wavefront sensor and producing therefrom a set of parameters describing surfaces of structures internal to the target optical system.

43. A method of measuring aberrations of a three-dimensional structure of a target optical system, comprising:
   creating a light beam;
   scanning the light beam in a plurality of desired directions;
   providing the scanned light beam onto a plurality of different locations in the target optical system; and
   receiving scattered light from each of the different locations.

44. The method of claim 43, further comprising:
   detecting wavefront data from the scattered light; and
   processing the detected wavefront data to determine therefrom a set of parameters describing surfaces of structures internal to the target optical system.

45. The method of claim 44, wherein processing the detected wavefront data to determine therefrom a set of parameters describing surfaces of structures internal to the target optical system includes using a priori information regarding the internal structures increase an accuracy of the determined set of parameters.

46. The method of claim 43, wherein the target optical system is an eye, and further comprising:
   performing a corneal topography measurement of the eye;
   detecting wavefront data from the scattered light; and
   processing the detected wavefront data to determine therefrom a set of parameters describing surfaces of internal structures of the eye,
   wherein processing the detected wavefront data includes using corneal surface parameters from the corneal topography measurement to increase an accuracy of the determined set of parameters.

47. A tomographic wavefront analysis system for measuring a target optical system, comprising:
   means for creating a plurality of light beams;
   means for optically imaging the light beams and projecting the light beams onto a plurality of different locations in the target optical system; and
   means for receiving scattered light from each of the locations and detecting individual wavefronts of the scattered light.

48. The system of claim 47, wherein the means for optically imaging the light beams and projecting the light beams onto a plurality of different locations in the target optical system comprises means for simultaneously imaging the light beams and projecting the light beams onto a plurality of different locations in the target optical system.

49. The system of claim 48, wherein the means for creating a plurality of light beams comprises means for producing the plurality of light beams having substantially a same wavelength.

50. The system of claim 49, wherein the means for producing the plurality of light beams having substantially a same wavelength comprises a plurality of laser diodes.

51. The system of claim 49, wherein the means for receiving scattered light from each of the locations and detecting individual wavefronts of the scattered light includes means for spatially separating the received scattered light.

52. The system of claim 51, wherein the means for receiving scattered light from each of the locations and detecting individual wavefronts of the scattered light includes:
   a lenslet array having a first number of lenslets receiving and focusing the scattered light; and
   a detector array having a second number of pixels detecting the focused scattered light,
   wherein the second number is substantially greater than the first number.

53. The system of claim 48, wherein the means for creating a plurality of light beams comprises means for producing the plurality of light beams each having a corresponding different wavelength.

54. The system of claim 53, wherein the means for producing the plurality of light beams each having a corresponding different wavelength comprises:
   a broadband light source creating light having a plurality of wavelengths;
   an angularly tuned filter receiving the light and producing therefrom the plurality of light beams each having a corresponding different wavelength, each said light beam being projected at a different angle from the angularly tuned filter.

55. The system of claim 53, the means for receiving scattered light from each of the locations and detecting individual wavefronts of the scattered light includes means for spectrally separating the received scattered light.

56. The system of claim 55, wherein the means for receiving scattered light from each of the locations and detecting individual wavefronts of the scattered light includes:

a lenslet array receiving and focusing the scattered light; and a detector array having a mosaic pattern of color-coded pixels detecting the focused scattered light, wherein each color-coded pixel substantially detects only light corresponding to one of the different wavelengths.

57. The system of claim 55, wherein the wavefront sensor comprises a plurality of detector arrays, each of the detector arrays being color-coded to substantially detect only light corresponding to one of the different wavelengths.

58. The system of claim 47, wherein the means for optically imaging the light beams and projecting the light beams onto a plurality of different locations in the target optical system comprises means for sequentially imaging the light beams and projecting the light beams onto a plurality of different locations in the target optical system.

59. The system of claim 58, wherein the means for creating a plurality of light beams comprises a scanning mirror.

60. The system of claim 58, further comprising a light valve disposed in an optical path between the target optical system and the means for receiving scattered light from each of the locations and detecting individual wavefronts of the scattered light, the light valve sequentially passing the scattered light to the means for receiving scattered light from each of the locations and detecting individual wavefronts of the scattered light.

61. The system of claim 47, further comprising means for receiving detected wavefront data and determining therefrom a set of parameters describing surfaces of structures internal to the target optical system.

62. A wavefront sensor for a wavefront analysis system, comprising:

a lenslet array receiving and focusing scattered light; and a plurality of detector arrays located at different detector planes and detecting the focused scattered light from the lenslet array, wherein each of the detector arrays is color-coded to substantially detect only light corresponding to a different corresponding wavelength.

63. The wavefront sensor of claim 62, further comprising at least one spectral filter disposed in an optical path between the lenslet array and the detector arrays, the spectral filter spectrally filtering the focused scattered light provided to the detector arrays.

64. A wavefront sensor for a wavefront analysis system, comprising:

a lenslet array receiving and focusing scattered light; and a detector array having a mosaic pattern of color-coded pixels detecting the focused scattered light.

65. A tomographic wavefront analysis system, comprising:

a projection system creating a light beam;

a fixation target sequentially focusing the eye in a plurality of different directions;

an optical imaging system receiving the light beam and providing the light beam sequentially onto a plurality of different locations on a retina of the eye corresponding to the different directions in which the eye is focused by the fixation target; and a wavefront sensor receiving scattered light from each of the different locations.

66. The system of claim 65, further comprising a processor receiving data from the wavefront sensor and producing therefrom a set of parameters describing surfaces of structures internal to the eye.

67. A method of measuring aberrations of a three-dimensional structure of an eye, comprising:

creating a light beam;

sequentially focusing the eye in a plurality of different directions providing the light beam sequentially onto a plurality of different locations on a retina of the eye corresponding to the different directions in which the eye is focused by the fixation target; and receiving scattered light from each of the different locations.

68. The method of claim 67, further comprising:

detecting wavefront data from the scattered light; and processing the detected wavefront data to determine therefrom a set of parameters describing surfaces of structures internal to the eye.

69. The method of claim 68, wherein processing the detected wavefront data to determine therefrom a set of parameters describing surfaces of structures internal to eye includes using a priori information regarding the internal structures increase an accuracy of the determined set of parameters.

70. The method of claim 67, further comprising:

performing a corneal topography measurement of the eye;

detecting wavefront data from the scattered light; and processing the detected wavefront data to determine therefrom a set of parameters describing surfaces of internal structures of the eye, wherein processing the detected wavefront data includes using corneal surface parameters from the corneal topography measurement to increase an accuracy of the determined set of parameters.

* * * * *